US00PP17921P2

(12) United States Plant Patent
Schräder

(10) Patent No.: US PP17,921 P2
(45) Date of Patent: Aug. 14, 2007

(54) ***VERBENA* PLANT NAMED 'SUMVERB 13'**

(50) Latin Name: *Verbena hybrida*
Varietal Denomination: Sumverb 13

(76) Inventor: Ralf Schräder, Karl-Leisner-Str. 15, D-59348 Lüdinghausen (DE)

( * ) Notice: Subject to any disclaimer, the term of this patent is extended or adjusted under 35 U.S.C. 154(b) by 0 days.

(21) Appl. No.: 11/323,156

(22) Filed: Dec. 30, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

GTITM UPOVROM Citation for 'Sumverb 13' as per QZ PBR 20041068; Aug. 15, 2004.*

* cited by examiner

*Primary Examiner*—Kent Bell
(74) *Attorney, Agent, or Firm*—C. A. Whealy

(57) ABSTRACT

A new and distinct cultivar of *Verbena* plant named 'Sumverb 13', characterized by its outwardly spreading and cascading plant habit; vigorous growth habit; early and freely flowering habit; and large red purple-colored flowers.

2 Drawing Sheets

Botanical designation: *Verbena hybrida.*
Cultivar denomination: 'Sumverb 13'.

BACKGROUND OF THE INVENTION

The present Invention relates to a new and distinct cultivar of *Verbena* plant, botanically known as *Verbena hybrida,* and hereinafter referred to by the name 'Sumverb 13'.

The new *Verbena* is a product of a planned breeding program conducted by the Inventor in Lüdinghausen, Germany. The objective of the breeding program is to develop new vigorous *Verbena* cultivars with large and intensely-colored flowers.

The new *Verbena* originated from a cross-pollination made by the Inventor in March, 2002 of a proprietary seedling selection of *Verbena hybrida* identified as Seedling 12, not patented, as the female, or seed, parent with a proprietary seedling selection of *Verbena hybrida* identified as Seedling 1, not patented, as the male, or pollen, parent. The cultivar Sumverb 13 was discovered and selected by the Inventor as a flowering plant within the progeny from the aforementioned cross-pollination in a controlled environment in Lüdinghausen, Germany in September, 2002.

Asexual reproduction of the new cultivar by cuttings at Lüdinghausen, Germany, since October, 2002, has shown that the unique features of this new *Verbena* are stable and reproduced true to type in successive generations of asexual reproduction.

SUMMARY OF THE INVENTION

The following traits have been repeatedly observed and are determined to be the unique characteristics of 'Sumverb 13'. These characteristics in combination distinguish 'Sumverb 13' as a new and distinct cultivar:

1. Outwardly spreading and cascading plant habit.
2. Vigorous growth habit.
3. Early and freely flowering habit.
4. Large red purple-colored flowers.

Plants of the new *Verbena* differ from plants of the female parent selection in the following characteristics:

1. Plants of the new *Verbena* flower earlier than plants of the female parent selection.
2. Plants of the new *Verbena* have larger flowers than plants of the female parent selection.

Plants of the new *Verbena* differ from plants of the male parent selection in the following characteristics:

1. Plants of the new *Verbena* are more compact than plants of the male parent selection.
2. Plants of the new *Verbena* are more cascading than plants of the male parent selection.

The new *Verbena* can be compared to the cultivar, Sunvivaro, disclosed in U.S. Plant Pat. No. 13,724. However, in side-by-side comparisons conducted in Lüdinghausen, Germany, plants of the new *Verbena* differed from plants of the cultivar Sunvivaro in the following characteristics:

1. Plants of the new *Verbena* were larger than plants of the cultivar Sunvivaro.
2. Plants of the new *Verbena* were more cascading than and not as upright as plants of the cultivar Sunvivaro.
3. Plants of the new *Verbena* were more freely branching than plants of the cultivar Sunvivaro.
4. Plants of the new *Verbena* flowered earlier than plants of the cultivar Sunvivaro.
5. Plants of the new *Verbena* were more freely flowering than plants of the cultivar Sunvivaro.
6. Plants of the new *Verbena* had larger inflorescences and larger flowers than plants of the cultivar Sunvivaro.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Verbena*.

The photograph on the first sheet comprises a side perspective view of a typical plant of 'Sumverb 13' grown in a container.

The photograph on the second sheet is a close-up view of typical flowers of 'Sumverb 13'.

DETAILED BOTANICAL DESCRIPTION

In the following description, color references are made to The Royal Horticultural Society Colour Chart, 2001 Edition, except where general terms of ordinary dictionary significance are used. Plants grown in 37-cm containers were used for the aforementioned photographs and following description. Plants had been growing for about four months when the photographs and the description were taken. Plants were grown under conditions which closely approximate commercial production conditions during the spring and summer in Lüdinghausen, Germany in an outdoor nursery. During the production period, day temperatures ranged from about 16° C. to about 30° C. and night temperatures ranged from about 8° C. to about 14° C.

Botanical classification: *Verbena hybrida* cultivar Sumverb 13.

Parentage:

*Female parent.*—Proprietary seedling selection of *Verbena hybrida* identified as Seedling 12, not patented.

*Male parent.*—Proprietary seedling selection of *Verbena hybrida* identified as Seedling 1, not patented.

Propagation:

*Type cutting.*—Vegetative tip cuttings.

*Time to initiate roots, summer.*—About 14 days at 16° C.

*Time to initiate roots, winter.*—About 18 days at 16° C.

*Time to develop roots, summer.*—About 24 days at 16° C.

*Time to develop roots, winter.*—About 28 days at 16° C.

*Root description.*—Fine, fibrous; color, 162C.

*Rooting habit.*—Freely branching; moderately dense.

Plant description:

*General appearance.*—Outwardly spreading and cascading plant habit; mounded and bushy plant form.

*Growth and branching habit.*—Freely basal branching; about ten lateral branches develop per plant. Pinching, that is, removal of the terminal apices, enhances branching with lateral branches potentially forming at every node. Vigorous growth habit.

*Plant height.*—About 30 cm.

*Plant diameter or spread.*—About 40 cm.

*Lateral branch description.*—Length: About 25 cm. Diameter: About 4 mm to 5 mm. Internode length: About 2 cm to 2.8 cm. Texture: Pubescent. Color: 146B.

*Foliage description.*—Arrangement: Opposite, simple. Length: About 3 cm to 4.5 cm. Width: About 1.5 cm to 2.5 cm. Shape: Lanceolate. Apex: Acute. Base: Cordate. Margin: Crenate. Texture, upper and lower surfaces: Slightly pubescent. Venation pattern: Pinnate. Color: Developing foliage, upper surface: 138B. Developing foliage, lower surface: 138A to 138B. Fully expanded foliage, upper surface: 137A. Fully expanded foliage, lower surface: 137B to 137C. Venation, upper and lower surfaces: 146D. Petiole: Length: About 2 mm. Diameter: About 1 mm. Texture, upper and lower surfaces: Smooth. Color, upper and lower surfaces: 146D.

Flower description:

*Flower type and habit.*—Single upright salverform flowers arranged on hemispherical corymbs. Freely flowering with about 20 to 25 flowers and flower buds per inflorescence. Inflorescences positioned above and beyond the foliage. Flowers last about one week on the plant. Corollas not persistent. Flowers slightly fragrant.

*Flowering season.*—In the garden, flowering is continuous from early spring until fall. Early flowering, plants begin flowering about four to five weeks after pinching.

*Inflorescence height.*—About 4 cm to 5 cm.

*Inflorescence diameter.*—About 4 cm to 4.5 cm.

*Flower size.*—Diameter: About 2.3 cm to 2.5 cm. Height (depth): About 2 cm to 2.2 cm.

*Flower buds.*—Length: About 1 cm to 1.2 cm. Diameter: About 3 mm. Shape: Elongate oblong. Color: N78A.

*Petals.*—Quantity/arrangement: Five per flower fused at base. Length: About 1.3 cm to 1.6 cm. Width: About 1 cm to 1.2 cm. Shape: Roughly cordate. Apex: Emarginate. Margin: Entire. Texture, upper and lower surfaces: Glabrous, smooth; velvety. Color: When opening, upper surface: 53A to 53C. When opening, lower surface: 71B to 71C. Fully opened, upper surface: N57A to N57C; color becoming closer to light pink with development. Fully opened, lower surface: N66C to N66D.

*Sepals.*—Number: Calyx is five parted. Quantity/arrangement: Five, fused into an elongated tube. Length: About 1.2 cm. Diameter: Less than 1 mm. Shape: Lanceolate. Apex: Acute. Margin: Entire. Texture, upper and lower surfaces: Smooth. Color, immature, upper and lower surfaces: 138A. Color, mature, upper surface: 138A. Color, mature, lower surface: 137C.

*Peduncles.*—Length: About 3 mm. Diameter: About 1 mm. Strength: Strong. Angle from stem: About 35° to 45°. Texture: Smooth. Color: 137A.

*Reproductive organs.*—Stamens: Quantity: Five per flower. Anther shape: Oblong. Anther length: Less than 1 mm. Anther color: 17B. Pollen amount: Scarce. Pollen color: 17B. Pistils: Quantity: One per flower. Pistil length: About 2 mm. Style length: About 1 cm. Style color: 17B. Stigma shape: Bi-parted. Stigma color: 17B. Ovary color: Close to 145A.

*Seeds.*—Length: About 1 mm to 2 mm. Diameter: About 1 mm. Color: 202A.

Disease/pest resistance: Plants of the new *Verbena* have not been observed to be resistant to pathogens and pests common to *Verbena*.

Temperature tolerance: Plants of the new *Verbena* have been observed to be tolerant to temperatures ranging from about 0° C. to about 40° C.

It is claimed:

1. A new and distinct cultivar of *Verbena* plant named 'Sumverb 13', as illustrated and described.

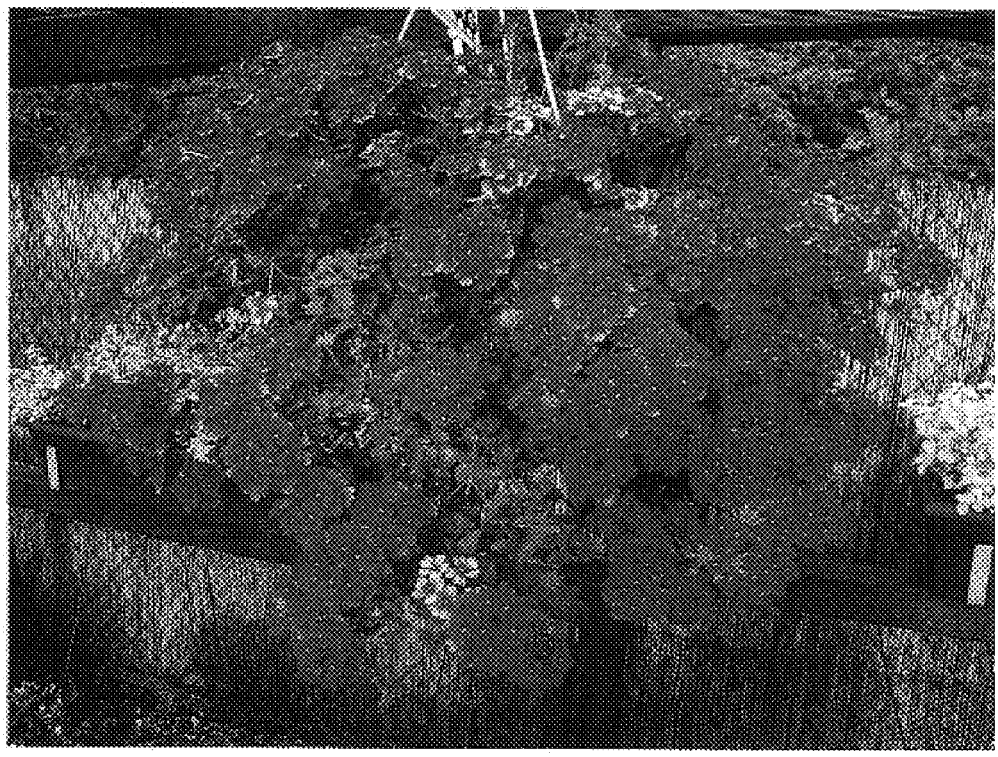

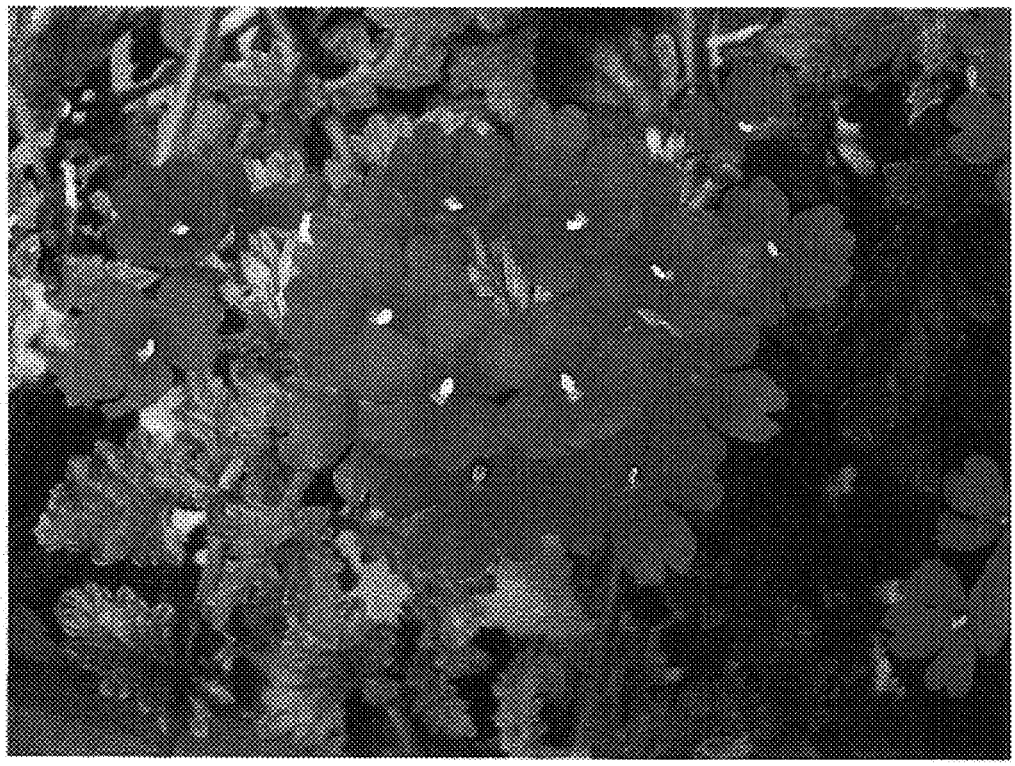

* * * * *